US00PP30101P2

(12) United States Plant Patent
Pineau

(10) Patent No.: US PP30,101 P2
(45) Date of Patent: Jan. 15, 2019

(54) ***HIBISCUS* PLANT NAMED 'MINDOUR1'**

(50) Latin Name: *Hibiscus syriacus*
Varietal Denomination: MINDOUR1

(71) Applicant: HORTIVAL DIFFUSION SAS, Beaufort-en-Anjou (FR)

(72) Inventor: Patrick Pineau, Saint Mathurin sur Loire (FR)

(73) Assignee: PEPINIERES MINIER SA, Beaufort en Vallee (FR)

( * ) Notice: Subject to any disclaimer, the term of this patent is extended or adjusted under 35 U.S.C. 154(b) by 0 days.

(21) Appl. No.: 15/530,127

(22) Filed: Dec. 5, 2016

(51) Int. Cl.
*A01H 5/02* (2018.01)

(52) U.S. Cl.
USPC ..... Plt./257

(58) Field of Classification Search
USPC ..... Plt./257
See application file for complete search history.

*Primary Examiner* — Keith O. Robinson
(74) *Attorney, Agent, or Firm* — Penny J. Aguirre

(57) ABSTRACT

A new cultivar of *Hibiscus* named 'MINDOUR1', characterized by its large sized double flowers that are red-purple in color, its sterile flowers, its upright plant habit and its vigorous growth habit.

2 Drawing Sheets

Botanical classification: *Hibiscus syriacus*.
Cultivar designation: 'MINDOUR1'

CROSS REFERENCE TO RELATED APPLICATIONS

This application is co-pending with a U.S. Plant Patent Application filed for a plant derived from the same breeding program entitled *Hibiscus* Plant Named 'MINDOUV5' (U.S. Plant patent application Ser. No. 15/530,126). This application is related to a European plant breeders' rights application filed on Jun. 2, 2014, application No. 2014/4145. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Hibiscus* plant, botanically known as *Hibiscus syriacus* 'MINDOUR1', and will be referred to hereafter by its cultivar name, 'MINDOUR1'. 'MINDOUR1' is a new cultivar of Rose of Sharon, a deciduous shrub grown for use as a landscape plant.

The new cultivar of *Hibiscus* arose from a breeding program conducted by the Inventor in La Menitre, France. 'MINDOUR1' originated as a seedling that arose from seed planted from open pollination of a plant of *Hibiscus syriacus* from the Inventor's breeding program, reference no. 3436, as the female parent (not patented). The male parent is unknown. 'MINDOUR1' was selected as a single unique plant in 2011 from the resulting seedlings from the above cross.

Asexual propagation of the new cultivar was first accomplished by grafting in La Menitre, France in 2012 by the Inventor. Asexual propagation by grafting and stem cuttings has determined that the characteristics of the new cultivar are stable and are reproduced true to type in successive generations.

SUMMARY OF THE INVENTION

The following traits have been repeatedly observed and represent the characteristics 'MINDOUR1'. These attributes in combination distinguish 'MINDOUR1' as a new and distinct cultivar of *Hibiscus*.

1. 'MINDOUR1' exhibits large sized double flowers that are red-purple in color.
2. 'MINDOUR1' exhibits sterile flowers.
3. 'MINDOUR1' exhibits an upright plant habit.
4. 'MINDOUR1' exhibits a vigorous growth habit.

The female parent plant, '3436', differs from 'MINDOUR1' in having flowers that are lighter red-purple in color, less double and fertile. 'MINDOUR1' can be most closely compared to *Hibiscus syriacus* cultivars 'Duc de Brabant' (not patented) and 'MINDOUV5'. 'Duc de Brabant' is similar to 'MINDOUR1' in having flowers that are red-purple in color. 'Duc de Brabant' differs from 'MINDOUR1' in having a less vigorous growth habit, flowers that are smaller in size and lighter red-purple in color and leaf blades that are shorter in length. 'MINDOUR5' is similar to 'MINDOUV1' in have large double and sterile flowers and in having a vigorous growth habit. 'MINDOUR1' differs from 'MINDOUV5' in having flowers that are purple in color.

BRIEF DESCRIPTION OF THE DRAWINGS

The accompanying colored photographs illustrates the overall appearance and distinct characteristics of the new *Hibiscus*. The photographs were taken of plants 4 years in age as grown outdoors in Menitre, France.

The photograph in FIG. 1 provides a side view of 'MINDOUR1' in bloom.

Figure 1:
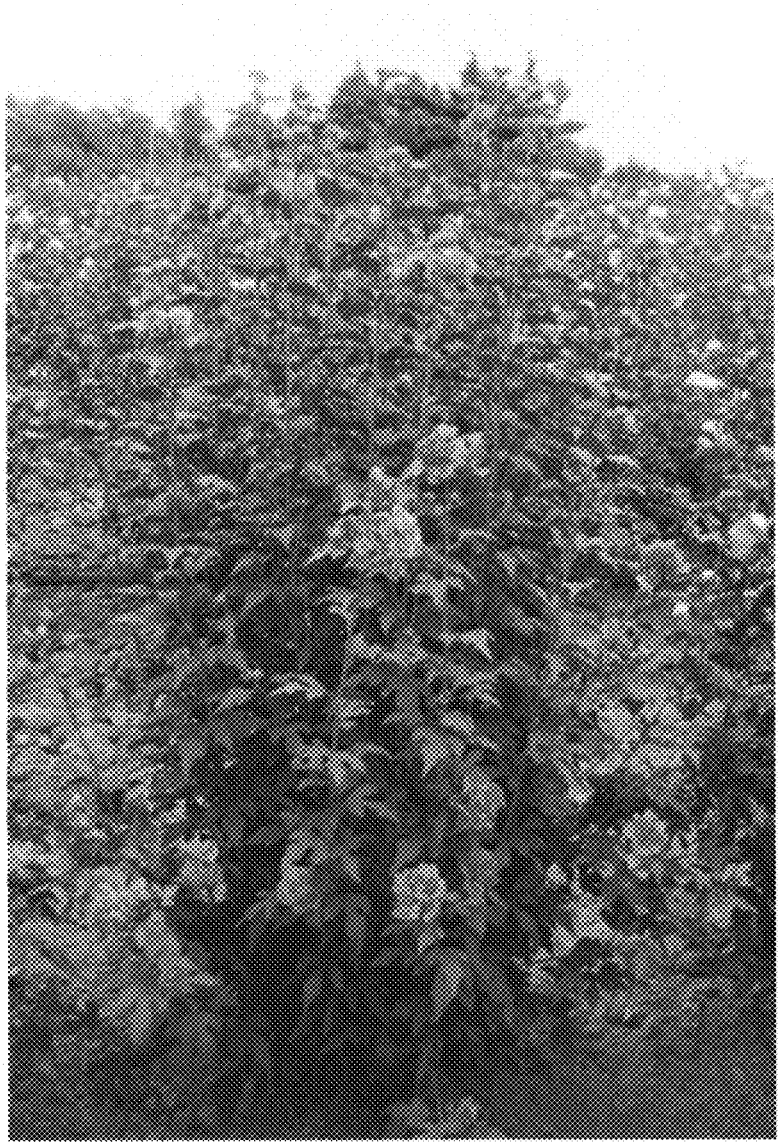
Figure 2:
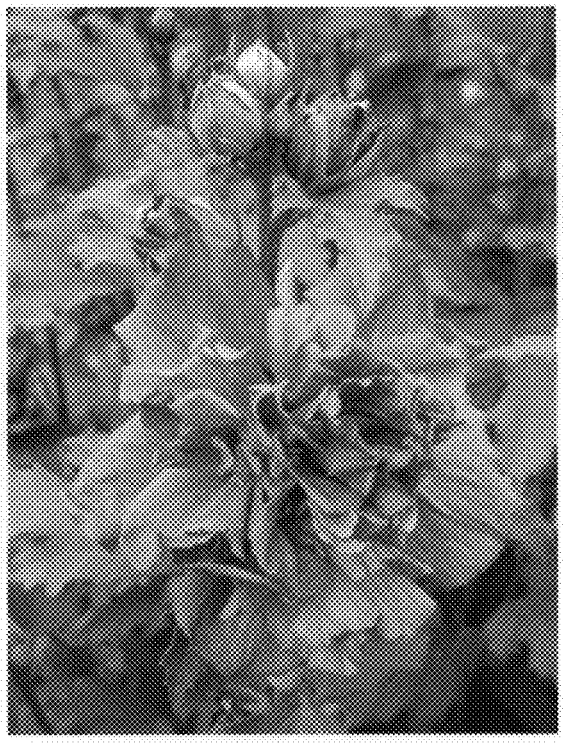

The photograph in FIG. 2 provides a close-up view of the flower and flower buds of 'MINDOUR1'.

Figure 3:
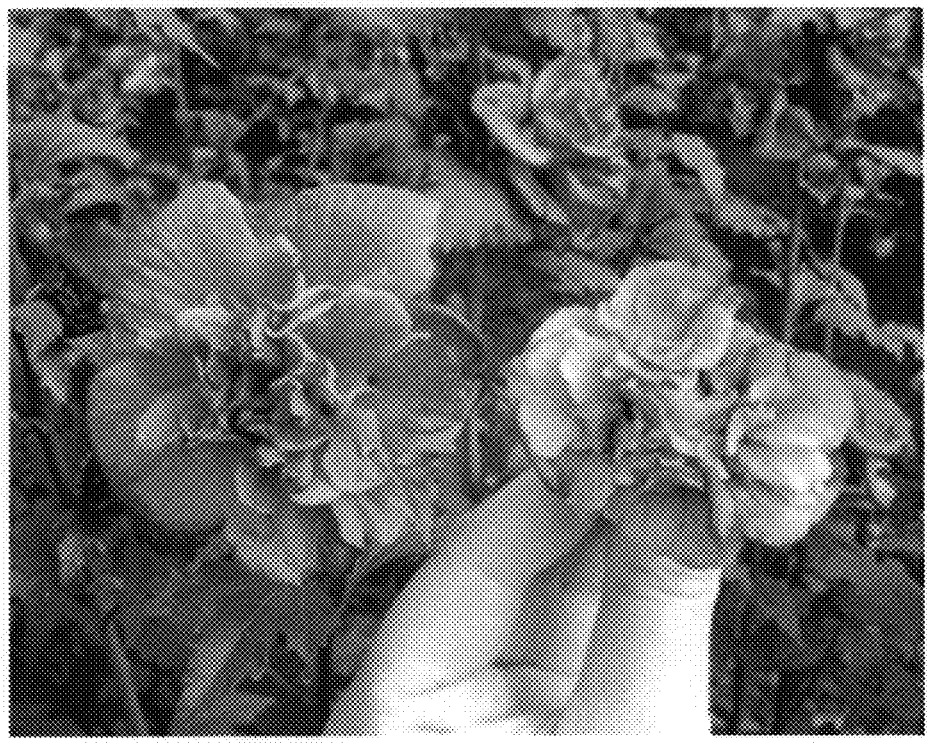

The photograph in FIG. 3 provides a comparison between a flower of 'MINDOUR1' on the left and a flower of 'Duc de Brabant' on the right.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 4 year-old plants of the new cultivar as grown in two-gallon containers in a greenhouse and outdoors in St Paul, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—8 weeks from mid summer to early autumn in La Menitre, France.

*Plant type.*—Deciduous shrub.

*Plant habit.*—Upright.

*Height and spread.*—Reaches 1.6 m in height and 70 cm in spread as a 4 year-old plant in the landscape.

*Hardiness.*—At least to U.S.D.A. Zone 4.

*Diseases.*—No susceptibility or resistance to diseases has been observed.

*Root description.*—Fleshy roots (4 mm in diameter), a blend of 138B and 159A in color, fibrous roots from fleshy roots; 164D in color.

*Root development.*—About 33 days to produce a young rooted plant from a graft.

*Propagation.*—Grafting.

*Growth rate.*—Vigorous.

Stem description:

*Shape.*—Slightly oval to round.

*Stem color.*—New growth; 143A lateral and secondary stems, mature wood; a blend of 197A and 195A.

*Stem size.*—Main stem; an average of 18 cm in length and 3 cm in width, lateral stems; an average of 30 cm in length and 1 cm in diameter, secondary stems; an average of 45 cm in length and 3 mm in width.

*Stem surface.*—New growth; pubescent, maturing wood; smooth with striations.

*Stem aspect.*—Held upright with secondary stems held about 15° to vertical.

*Stem strength.*—Very strong.

*Branching.*—An average of 1 main stem, 7 lateral stems, and 2 to 3 secondary stems per lateral branch.

*Internode.*—Average of 4 cm.

*Lenticels.*—158A in color, an average of 30 per stem section that is 3 cm in length and 1 cm in width, roughly orbicular in shape, 1 mm in diameter.

Foliage description:

*Leaf shape.*—Ovate to broadly lanceolate overall.

*Leaf division.*—Simple or 3-leaved.

*Leaf base.*—Cuneate.

*Leaf apex.*—Acute.

*Leaf venation.*—Pinnate, color matches leaf coloration.

*Leaf margins.*—Tri-lobed, deeply lobed, upper part of all lobes are serrate to crenate with lower part entire.

*Leaf attachment.*—Petiolate.

*Leaf arrangement.*—Alternate.

*Leaf orientation.*—Held downward to vertical.

*Leaf aspect.*—Slightly cupped inward to flat.

*Leaf surface.*—Very finely puberulent on upper and lower surface (appears glabrous).

*Leaf color.*—Young and mature leaves; upper surface and lower surface 146A, variegation absent.

*Leaf size.*—Average of 11 cm in length and 6 cm in width when 3-leaved and an average of 5 cm in length and 4 cm in width when simple.

*Leaf quantity.*—Average of 24 leaves per lateral branch 42 cm in length.

*Petioles.*—Average of 4 cm in length and 3 mm in diameter, 137B in color, pubescent surface.

*Stipule.*—2 at the base of each petiole, 5 mm in length, 1 mm in width, round in shape, pointed apex, glabrous surface, 146A in color.

Flower description:

*Inflorescence type.*—Fully double flowers in clusters of 3 to 5 at terminus.

*Inflorescence size.*—With one flower open and 2 buds an average of 12 cm in width and 7 cm in height.

*Lastingness of flowers.*—About 5 days, self cleaning.

*Flower size.*—An average of 3 cm in depth and 7 cm in diameter.

*Flower fragrance.*—None.

*Flower shape.*—Carnation-like.

*Flower number.*—An average of 3 to 5 per lateral stem.

*Flower aspect.*—Upright to outward.

*Flower bud.*—Elliptic-globose in shape, an average of 2 cm in length and 1.4 cm width, 138B in color.

*Flower attachment.*—Peduncle.

*Petal and petaloid number.*—Average of 5 petals and 35 petaloid stamens.

*Petal and petaloid shape.*—Petals; orbicular to broadly oblanceolate to elliptic, petaloid stamen; range from oblong to elliptic to oblanceolate.

*Petal and petaloid stamen color.*—Upper surface when newly opening; a blend of N79A and N79C and N80D, eye zone; is a blend of 202A and N79C, veins are N80D, lower surface when newly opening; a blend of N79A and N79C and N80D, base is NN155A with an eye zone that is a blend of 202A and N79A, veins are NN155A, fully open upper surface; a blend of 73A and N57D, eye zone at the base is mostly 60A, sometimes there are streaks of NN155C, fully open lower surface; a blend of 73A and 73C and N57D, base is NN155C with a petal spot at the base that is 60A, veins are NN155C, eye zones small and with extensions about 1.5 mm in length.

*Petal and petaloid stamen surface.*—Both surfaces smooth and dull, center petals are glossy.

*Petal and petaloid stamen margins.*—Wavy, medium undulation curled to entire.

*Petal attitude.*—Outer most petals slightly ascending.

*Petal and petaloid stamen apex.*—Rounded to wavy to notched.

*Petal and petaloid stamen base.*—Cuneate.

*Petal and petaloid stamen size.*—Petals; up to 3 cm in length and 3 cm in width, petaloid stamens; ranging between 3 cm in length and 2 cm in width and 2 cm in length and 4 mm in width.

*Sepal number.*—5.

*Sepal shape*.—Triangular.

*Sepal margin*.—Entire.

*Sepal size*.—Average of 1.5 cm in length and 9 mm in width, free portion is triangular in shape and 6 mm in length.

*Sepal aspect*.—Upright.

*Sepal surface*.—Outer surface puberulent, inner surface glabrous and glossy.

*Sepal apex*.—Apiculate.

*Sepal base*.—80% of base is fused.

*Sepal color*.—Young and mature outer and inner surface; 138B.

*Calyx*.—Campanulate in shape, average of 1 mm in depth and 3 mm in diameter.

*Peduncles*.—An average of 6 mm in length and 3 mm in diameter, strong and stout, held upright to outward from stem, 139A in color, pubescent surface.

*Pedicels*.—Not present, flowers are solitary from peduncles attached to terminus.

*Bracts*.—7 to 9 bracts held close to calyx, linear in shape, apiculate apex, truncate base, average of 1 cm in length and 1 mm in width, a color 139A on inner and outer surface, inner and outer surface is pubescent.

Reproductive organs:

*Gynoecium*.—5 pistils, 1 cm in length, stigmas; 145C in color, puberulent surface, club shaped, and 3 mm in diameter, style; 145C in color and 4 mm in length, ovary; urn-shaped, 1 cm in length and 6 mm in width, 145C in color, pollen is minute and NN155C in color.

*Androecium*.—Stamens; some remain attached to the margins of the petaloid stamens in the center of the flower, average of 7, anther; 1 mm in diameter, flattened in ovoid in shape, 150D in color, some filaments observed extending below the petaloid stamen and average of 2, NN155C, 9 mm in length, smooth surface.

*Fruit/seeds*.—None produced.

It is claimed:

1. A new and distinct cultivar of *Hibiscus* plant named 'MINDOUR1' as herein illustrated and described.

* * * * *